United States Patent
Moreno et al.

(10) Patent No.: US 9,128,057 B2
(45) Date of Patent: Sep. 8, 2015

(54) DUAL-MODE MICROFLUIDIC GENETICS TESTING PLATFORMS AND METHODS OF DUAL-MODE GENETICS TESTING USING SAME

(75) Inventors: Tanya Moreno, San Diego, CA (US); Cindy Wang, San Diego, CA (US); David Becker, San Diego, CA (US)

(73) Assignee: Pathway Genomics Corporation, San Diego, CA (US)

(*) Notice: Subject to any disclaimer, the term of this patent is extended or adjusted under 35 U.S.C. 154(b) by 0 days.

(21) Appl. No.: 13/068,384

(22) Filed: May 10, 2011

(65) Prior Publication Data
US 2013/0011832 A1   Jan. 10, 2013

(51) Int. Cl.
*G01N 21/64* (2006.01)
*B01L 7/00* (2006.01)

(52) U.S. Cl.
CPC ............. *G01N 21/6452* (2013.01); *B01L 7/52* (2013.01)

(58) Field of Classification Search
CPC .................. B01J 2219/00722; B01L 3/5085; C12Q 1/6833; G01N 21/8483
See application file for complete search history.

(56) References Cited

U.S. PATENT DOCUMENTS

| | | | |
|---|---|---|---|
| 2005/0130183 A1* | 6/2005 | Oh et al. | 435/6 |
| 2008/0088952 A1* | 4/2008 | Unger et al. | 359/798 |
| 2008/0176290 A1* | 7/2008 | Joseph et al. | 435/91.2 |
| 2008/0274511 A1* | 11/2008 | Tan et al. | 435/91.2 |

OTHER PUBLICATIONS

Mayo et al "CNV analysis usning TaqMan copy number assays" Current Protocols in Human Genetics, Oct. 2010, 2.13: 1-10.*
Lee et al "Methods to detect and analyze copy number variations at the gnome-wide and locus-specific levels" Cytogenetic Genome Research 123: 333-342.*
Wu, Yee Ling, et al., 2007, "Sensitive and Specific Real-Time Polymerase Chain Reaction Assays to Accurately Determine Copy Number Variations (CNVs) of Human Complement C4A, C4B, C4-Long, C4-Short, and RCCX Modules: Elucidations of C4 CNVs in 50 Consanguineous Subjects with Defined HLA Genotypes", J Immunol, 179:3012-3025.

* cited by examiner

*Primary Examiner* — Betty Forman
(74) *Attorney, Agent, or Firm* — Knobbe Martens Olson & Bear LLP

(57) ABSTRACT

Dual mode genetics testing systems are devised about a single element testing platform. A microfluidic network and system of interconnected receiving cells and reaction vessels supports at the same time genotyping and copy number analysis where the platform may be subject to a common thermal cycle schedule to cause the proper reactions (DNA replication) necessary in both test types. Further, the microfluidic platform which includes reaction vessels for genotyping which are spatially removed from reaction vessels for copy number analysis, is coupled to optical scanner and detection systems specifically arranged to apply test specific detection routines on each of these distinct regions or portions of the dual mode test platform.

12 Claims, 7 Drawing Sheets

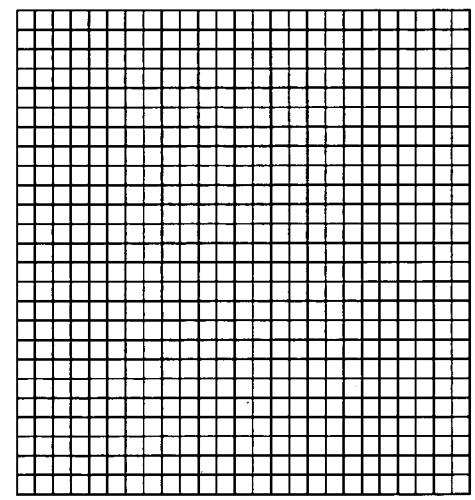
Fig 6A
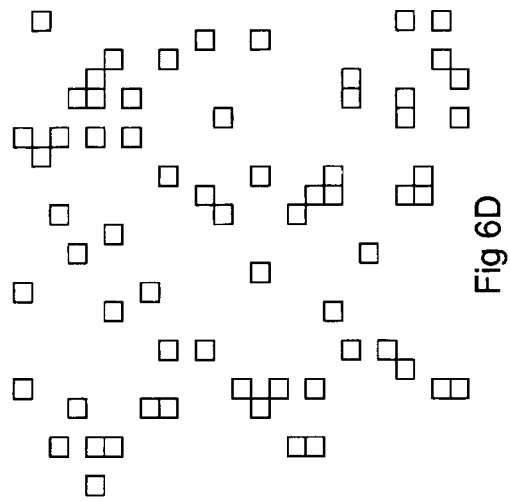
Fig 6B
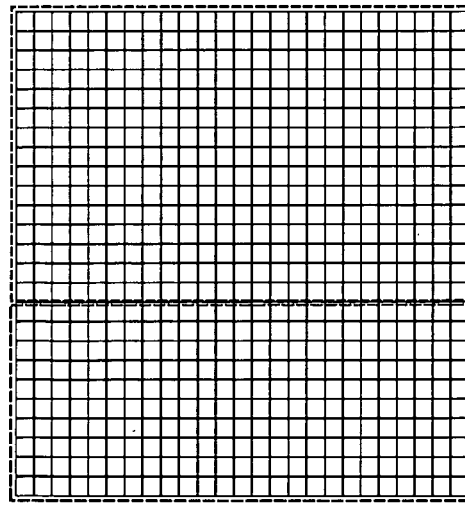
Fig 6C
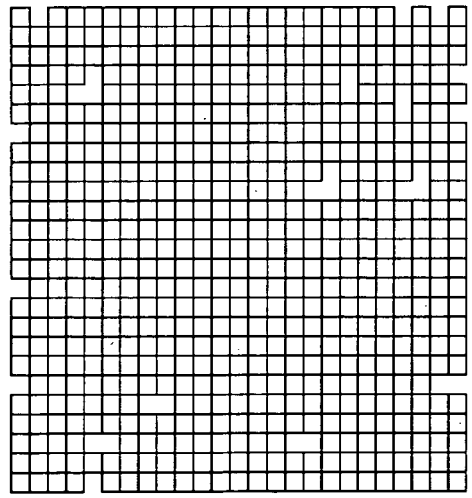
Fig 6D
FIG. 6

DUAL-MODE MICROFLUIDIC GENETICS TESTING PLATFORMS AND METHODS OF DUAL-MODE GENETICS TESTING USING SAME

BACKGROUND OF THE INVENTION

Field

The following invention disclosure is generally concerned with genetic testing and specifically concerned with genetics testing simultaneously in two modes including a sequencing mode and a copy number analysis mode.

Significant scientific advances in genetics processing technologies and have been aggressively developed by talented scientists in this modern era of genetic science advance. At the core of some of these technologies lie certain well-known and common processes including qPCR, 'TaqMan', among others. A push for efficiency and low cost continues to drive further improvement and each day new systems arrive which also improve our genetics testing capabilities.

In one special scenario of genetics testing strategy, it is important to perform both genotyping and copy number analysis genetic tests. This may be particularly the case with respect to a single genome because these two types of genetics tests rely on states of chemical reactions having somewhat different physical conditions and attributes, they were heretofore performed separately. Separate platforms were run in separate processes where distinct measurements were made for each test. But running separate tests for genotyping and copy number analysis is expensive in materials; consumes highly specialized equipment operation time; and requires significant skilled labor. It is thus highly desirable to perform both genotyping and copy number analysis in an single process run. This is especially the case when both genotyping and copy number analysis are to both be done on a single person's DNA or genome.

One most important platform for genetics testing is sometimes known as a "microfluidic genetics testing" system. Genetic samples and carefully prepared test chemistry (TaqMan) may be combined via a network of fluid channels to cause reactions between matter from both. Many forms of these arrays are now readily found in genetics testing laboratories everywhere.

SUMMARY OF THE INVENTION

Comes now, Tanya Moreno, Cindy Wang and David Becker with inventions of genetic testing systems including devices and methods for genetic sequencing and copy number determinations. It is a primary function of these systems to simultaneously and on a single platform provide for genetic measurements relating to both sequencing and copy number. It is a contrast to prior art methods and devices that systems first presented here do not require separate machine runs and independent processing. Rather, a single multiplex operation permits dual measurement types in a single well configured platform. Specifically, arrays of microfluidic reaction vessels are coupled to distinct optical detection means—each of two optical detection means directed to detection schemes for either sequencing or copy number determination.

A single microfluidic platform is arranged and devised along with its cooperating components and supporting apparatus, to perform both genotyping and copy number analysis in a single process run. An array of microfluidic cells and coupled fluid circuits forms a dual-mode genetics testing platform arranged to perform simultaneously genotyping and copy number analysis on a common genetics test sample set.

The microfluidic array is adapted to receive therein genetic matter from one or more individual test subjects of interest. In another portion of this dual-mode testing platform, chemistry or testing reagents may be received therein appropriately arranged receiving cells. So received, test chemistry is mixed with DNA matter after being brought together via a network of fluid channels to mix reaction vessels. Process steps including thermal cycles are performed while reagent chemistry and genetics matter under test are in a common cell to produce a reaction indicative of certain genetic states or conditions.

In one illustrative example version, in the portion of the test platform arranged to receive test chemistry, two distinct regions may be defined—each of these regions may include a plurality of receiving cavities into which reagents may be introduced. However, one first region associated with genotyping may receive a different chemical preparation than a second region associated with copy number analysis. The test chemistry for copy number analysis is distinct from and may sometimes be unsuitable for use in genotyping tests—and vice-a-versa. Accordingly, the portion of the microfluidic testing platform arranged to receive test chemistry is sometimes provided with two discrete and separate regions. One region each for each type of chemistry associated with genotyping and copy number analysis.

Dual-mode microfluidic test platforms first taught here are additionally arranged whereby they may be simultaneously coupled to a thermocycler and further coupled to optical detector systems. A thermocycler applies heat and cooling cycles in a highly regulated manner to the reaction vessels of the microfluidic platform to affect prescribed reactions between test DNA and reaction chemistry or chemistries. To bring about a high performance genotyping test, a particular heating/cooling schedule is necessary. Similarly, to bring about a copy number analysis a certain/cooling schedule is required. While heat/cooling cycles are sometimes quite similar and may in fact be identical under specific conditions, one important distinction with regard to the reaction vessels associated with copy number analysis, is that they must be optically interrogated between each thermal cycle (or set of thermal cycles) to properly measure the copy number or 'real-time PCR' signal. In genotyping, little or no information may be gained by measuring the reaction extent prior to completion of the thermal cycle schedule—by contrast, it is the end result after the entire set of thermal cycles are applied that is important to the genotype test. Yet it is impossible to attain copy number information at the end of the thermal cycle schedule without data taken throughout and during the thermal process.

Accordingly, special optical detector array systems are coupled to the reaction vessels by spatial division and spatial multiplexing. Such optical detector arrays include pluralities of optical detection elements in two distinct groups. A first group of optical detection elements is provided with amplification electronics which may drive the detector elements in accordance with the heat/cooling cycles to make a plurality of optical measurements throughout the course of thermocycler application. That is, this portion of the optical detection system is coupled to the thermal cycler. This first group of optical detection elements is associated with copy number analysis may be sometimes referred in the arts as 'qPCR' or 'real-time PCR'. These optical detection elements are coupled to corresponding reaction vessels which received the copy number reaction chemistry. Reaction vessels having therein the chemistry appropriate for genotyping are spatially separate from the copy number analysis reaction vessels and are thus physically coupled to a different optical detection system. An optical detection system suitable for genotyping measurement includes an amplifier and drive electronics which operate to make a single measurement at the end of the thermal cycle schedule. In addition, this optical detection system may also support advanced chromatic filtering whereby distinct colors of optical return signals may be addressed separately. In some genotyping systems, a single SNP may have either of a (major allele or minor allele) versions. In these cases, color is sometimes used to distinguish between these. There is no similar use of chromatic variation in the copy number portion of the optical detection and that optical detection system coupled to the copy number reaction vessels may be 'colorblind'.

Accordingly, systems first presented herein this disclosure are dual-mode genetics testing platforms of two portions, a first arranged to execute genotyping tests and a second suitably arranged to execute copy number testing. These both exist together in a single microfluidic platform and both types of tests may be executed together during a process thermal cycling and optical integration amenable to both distinct tests.

Such devices and systems are therefore well-positioned for cost savings and genetics testing improvements. Because a single platform is processed once with a group of DNA samples to produce both genotype and copy number data for each person under test on a single process run equipment, consumables and labor are significantly conserved.

The invention thus stands in contrast to methods and devices known previously. The invention includes a single apparatus and platform for carrying out these two important types of genetic tests and the tests may be executed simultaneously. Systems known today all belong to the body art which requires two separate processes including one process on one distinct platform for genetic sequencing and another process on another platform for copy number variation measurement. Heretofore, these tests are not made simultaneously on a single platform.

OBJECTIVES OF THE INVENTION

It is a primary object of the invention to provide new genetic testing systems.

It is an object of the invention to provide dual mode genetic testing systems based upon microfluidic reaction platforms.

It is a further object to provide microfluidic genetic testing platforms which operate simultaneously in a genotyping mode and a qPCR mode.

It is an object of the invention to provide dual mode microfluidic test platforms for genetics comprehensive genetics testing.

A better understanding can be had with reference to detailed description of preferred embodiments and with reference to appended drawings. Embodiments presented are particular ways to realize the invention and are not inclusive of all ways possible. Therefore, there may exist embodiments that do not deviate from the spirit and scope of this disclosure as set forth by appended claims, but do not appear here as specific examples. It will be appreciated that a great plurality of alternative versions are possible.

BRIEF DESCRIPTION OF THE DRAWING FIGURES

These and other features, aspects, and advantages of the present inventions will become better understood with regard to the following description, appended claims and drawings where:

FIG. 6 illustrates example spatial distributions which might be used in various alternative versions these systems.

PREFERRED EMBODIMENTS OF THE INVENTION

Figure 1:
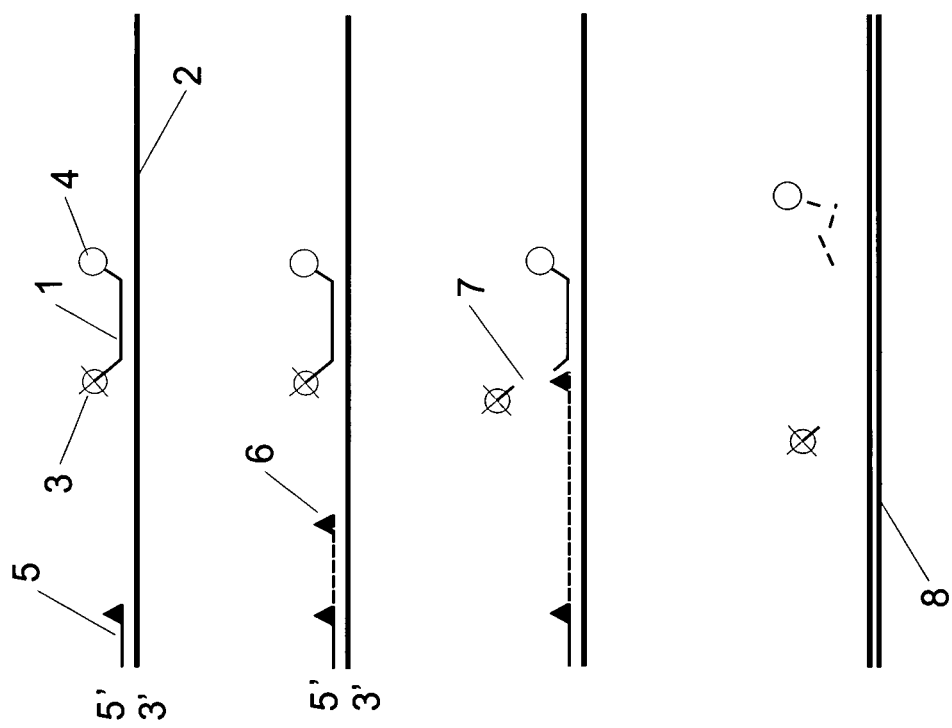
FIG. 1 is a prior art diagram illustrating a popular genetic testing reaction—TaqMan.

As an introduction to one important form of genetic testing, the reader will appreciate the brief review of TaqMan mechanics herefollowing. TaqMan probes 1 bind to a long strand of DNA 2. These probes include a complementary nucleotide combination with respect to the test DNA to which is binds. The probe additionally includes an optical marker or 'reporter' 3 and further an optical 'quencher' 4.

After test DNA is subjected to high temperature, it is denatured into two separate strands, the TaqMan probes can anneal themselves thereto at sites with matching oligos. As the chemistry cools further, a primer 5 anneals to the template DNA strand to form a complimentary strand. Taq polymerase 6 adds further nucleotides to the strand until it reaches the probe and eventually removes the probe from the template DNA and in the process separating 7 the reporter from the quencher. When illuminated, a free reporter will re-emit optical energy which can be detected by an optical sensor or scanner. Further replication of the PCR product is not interrupted by the probe. The newly formed double strand 8 is ready to be denatured again and the entire process repeated in further PCR cycles.

Figure 2:
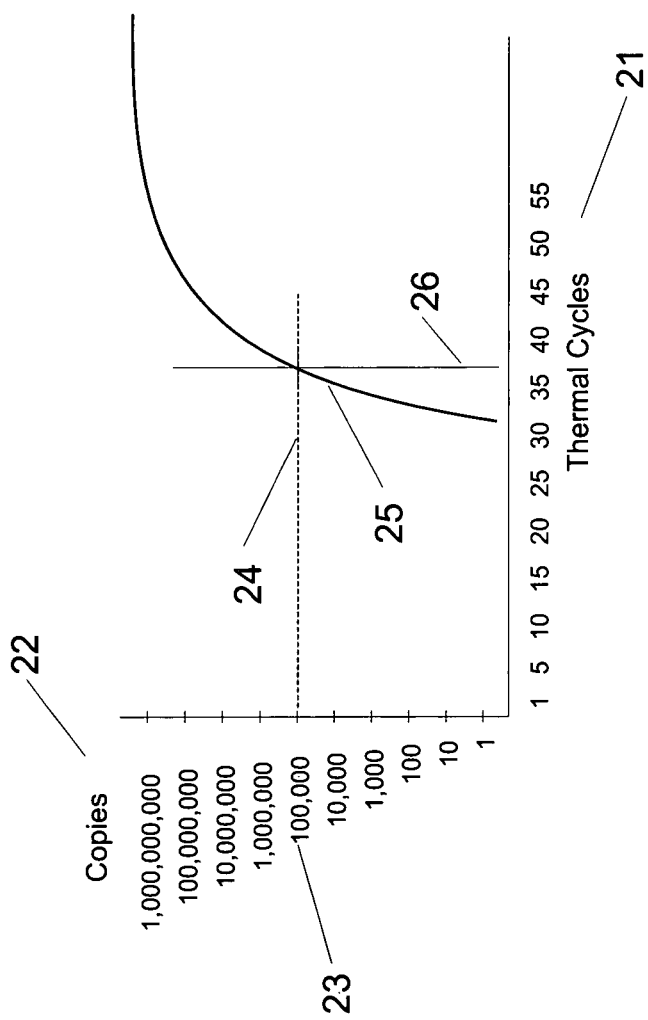
FIG. 2 is a chart diagram showing a return optical signal taken over the course of a TaqMan reaction process.

FIG. 2 illustrates a signal which is characteristic of a copy number analysis. In copy number testing, a DNA test sample is inserted into a receiving cell or a plurality of receiving cells of the testing platform designated for that purpose. A receiving cell arranged to receive the appropriate TaqMan reagent chemistry, a cell cooperatively coupled to the receiving cell in which the test DNA sample was received whereby matter received at these two cells are combined in a common reaction vessel having been previously mapped to a specific known location of the array platform whereby optical access is afforded. So combined, the chemistry is subjected to repeated heating and cooling cycles—or thermal cycles as illustrated in the drawing figure on the horizontal axis. As thermal cycles are processed, the DNA is replicated repeatedly and copies 22 (vertical axis of the chart) of the DNA are formed. In the case where specific conditions are met i.e. the TaqMan probe matches the test DNA and binds thereto, copies are produced and optical markers are cleaved away with every thermal cycle applied. Conversely, where the probe sequences are not found in the sample DNA, the replication process does not produce appreciable amounts of free optical reporters.

If the reaction vessels associated with copy number variation analysis are appropriately illuminated after thermal each cycle, a return optical signal from the free reporters proportional to the number of copies can be detected at optical detector elements arranged to detect same; i.e. optical detectors having a high intensity dynamic range. In some test systems, a prescribed number of copies e.g. 100,000 copies 23 may correspond to a threshold signal level 24. If the optical signal 25 returned from copy number analysis reaction vessels reaches the threshold level after a specific number of cycles 26, it is safe to draw a conclusion regarding the copy number for the test sample. This is due in part to a known reference cell run in parallel where the copy number is known. The relative intensities permits one to conclude copy number information about the test sequence. While this copy number analysis and technique may be well known in the art, and therefore it is not the purpose of this disclosure to detail qPCR, what is not known is using a microfluidic platform where various portions of the platform are simultaneously coupled to separate detection systems and technique. That is, where portions of the platform support copy number analysis and other portions of the platform are arranged to support genotyping for the same process run.

Figure 3:
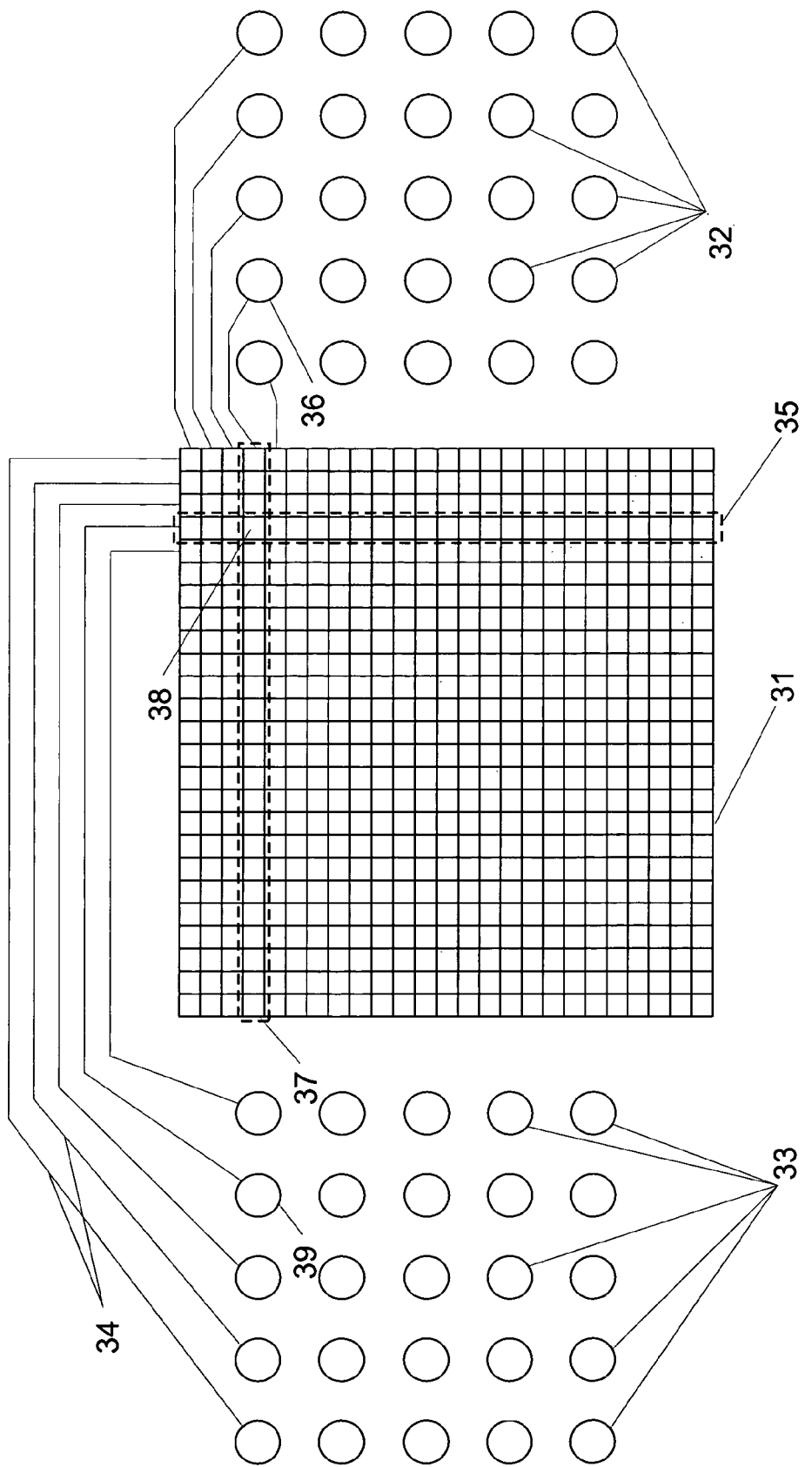
FIG. 3 is an illustrative first example of a test platform including an array of reaction vessels.
Figure 4:
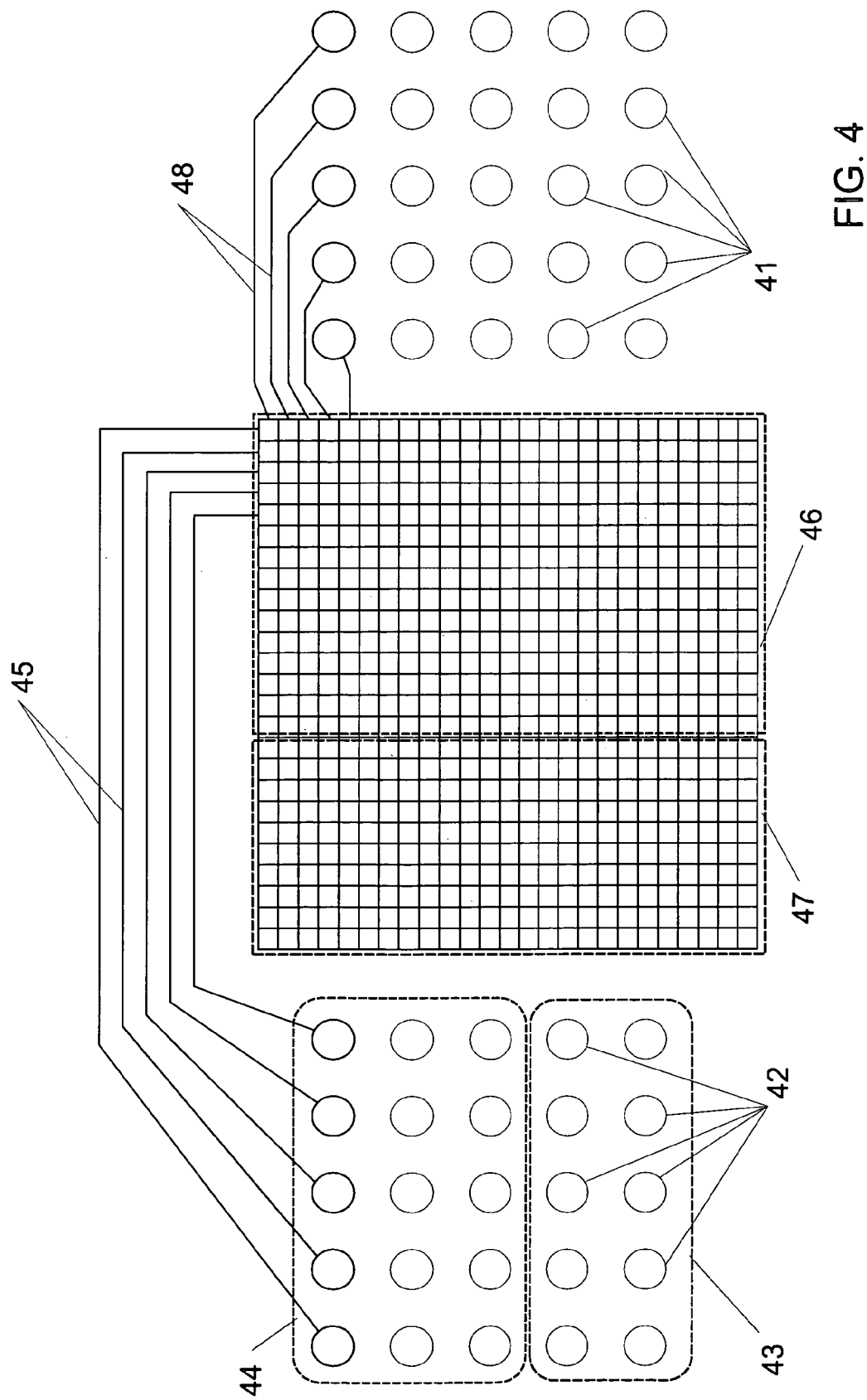
FIG. 4 is a line diagram representation of a dual mode genetics testing platform showing examples of receiving cells coupled to reaction cells.

This principle of a dual-mode microfluidic platform 31 arranged to support at the same time both genotype testing and copy number analysis testing is better understood in view of the drawing FIGS. 3 and 4. With reference to FIG. 3, a diagram which details a microfluidic network of coupled cells, receiving cells 32 are arranged to receive therein DNA samples to be tested. Samples of DNA from donors of interest may be inserted into these cells which operate as an input port of the microfluidic system. DNA which has been subject to preprocessing might include steps to stabilize, isolate or purify DNA samples. In addition, the DNA samples may be supported in a chemical medium amenable to DNA replication processes and conditions. Receiving cells 32 may be arranged to receive DNA from a single subject i.e. a single person, or arranged to receive DNA from, several persons. However, each cell typically supports receipt of DNA from a single organism (person).

Each of the receiving cells 32 (25 cells in the illustrative diagram) is coupled by way of tiny fluid channels to an array of reaction vessels in which chemistry from a plurality of sources (one DNA sample and one reaction reagent) may be mixed together and further in which chemical reactions may, be effected. Further, these reaction vessels are arranged whereby an optical probe and/or optical illumination beams may be received such that illumination light falls incident upon chemistry contained in the reaction vessel. Further, these reaction vessels are carefully coupled to optical detectors which operate to detect light radiated from the reaction chemistry in response to stimulation by illumination beams.

Receiving cells 33 are arranged to receive therein reagents used to support DNA replication reactions and DNA probes. In some preferred versions, there are at least two types of important modules arranged to receive these test reagents. Two distinct compositions of reagents, each composition supporting either of two types of processes. These include reagents which support genotype genetics testing methodology and reagents which support copy number analysis genetics testing.

These reagents are not mixed together in any single receiving cell, but rather are physically isolated—a reagents composition suitable for genotyping being put into receiving cells of the genotyping module and some another distinct composition of reagents being put into receiving cells of the copy number analysis module. In this way, we can assure spatial distinction between the two types of reactions being simultaneously carried out on the dual-mode platform.

Because relative intensity of return signals from a copy number module is critically important for accurate copy number determinations, it is useful to include in reagent chemistry a contrast enhancing solution. It is not necessary to include a contrast agent in the TaqMan used with the genotyping module because optical signals read there are thresholded and there is no range of intensities to be compared. A contrast agent does not improve the optical return signal in the genotyping channel of these optical detectors. Accordingly, only the reagents used in the copy number analysis module contain such contrast agent.

At least one reaction vessel of the copy number analysis module is reserved for a reference probe. When appropriate reagents are added to the copy number analysis module, these include genetic probes and a reference DNA strand. That is, one of the reaction vessels necessarily includes a genetic probe and reference oligo which will produce a replication reaction at a known rate. From this reference, all other optical signals of the copy number analysis module may be compared. Accordingly, reagents provided to the copy number analysis module also include this reference scheme. As the optical signals of the genotyping module are not compared in this way, compositions of reagents provided to the genotyping module do not include similar reference materials.

However, genotyping modules do sometimes require unique reagent chemistries. In some important versions, a genotyping reaction will include a plurality of distinct optical reporters. These optical reporters may be distinguished by their color. Each reporter may respond to the reaction process differently depending upon the precise nature of the SNP under test. In this way, different colors may be used to indicate the presence of various zygote forms. Reagent compositions used with the copy number analysis module does not benefit from the use of multi-colored reporters. As such, reagent compositions for each of the two modules may be distinct and these must be properly mapped in agreement with the spatial distribution schemes of these dual mode systems.

Receiving cells which support receipt therein of various reagent chemistry are coupled by way of microfluidic channels 34 to the array of reaction vessels. In some versions, a single receiving cell is coupled to each reaction vessel of an entire row of reaction vessels.

Similarly, a receiving cell 36 in receipt of DNA test matter may be coupled to each reaction vessel of an entire row 37 of reaction vessels. In this way, we can assure that a single DNA sample can be subjected to a large plurality of different reagent chemistries i.e. 25 in this example of FIG. 3. Reaction vessel 38 thus receives by way of the microfluidic channels the DNA sample from receiving cell 36 and reagent chemistry from receiving cell 39.

For a complete understanding of these systems, it is important to appreciate the nature of spatially distinguishing reaction vessels associated with the two types of genetics testing. A reaction vessel associated with either test type is chemically coupled by way of fluid channels to appropriate reagents and is further optically coupled to a discrete detection system most suitable for the particular test type. These dual-mode platforms must support simultaneous testing of two types via spatially distributed elements of an array of reaction vessels which together form a unitary platform. However, it is a necessary requirement that the appropriate chemistry and appropriate detection systems—for each genetics test type be properly mapped to the various reaction vessels. That is, a reaction vessel associated with genotype testing is coupled to the appropriate reaction chemistry and appropriate detection system by way of its unique mapped location in the array. Reaction vessels associated with copy number analysis similarly are coupled to appropriate reaction chemistry and an optical detection system suitable for copy number type measurements. Both types of reaction vessels, despite their spatial distribution and physical separation are thermally coupled to the same thermocycler system. It is not necessary in the two types of tests to apply different thermocycler schedules and a single thermal cycle schedule can be used to advance appropriate DNA replication in both genotype tests and copy number analysis tests. For this reason, these microfluidic platforms may be coupled at their underside to a single thermocycler which delivers identical heat/cooling cycles to both types of reaction vessels; i.e. there is no need for spatial distribution of heat application.

FIG. 4 presents in an example constructed for illustration purposes and ease of understanding, twenty-five receiving cells 41 are suitable for receiving therein DNA samples of either a single test subject or plurality of test subjects. Ten reagent receiving cells 42 distributed in a prescribed region 43 comprise receiving cells which support copy number analysis type genetics testing. A region 44 of fifteen receiving cells forms a microfluidic platform input port associated with genotype testing. Chemistry appropriate for genotype testing is received at cells in this region. Such receiving cells are coupled by fluid channels 45 whereby reagents received therein are conveyed to reaction vessels of the region 46 shown which form an array of 375 reaction vessels which support genotyping. An array of reaction vessels forms the region 47, these cells which are spatially removed and distinct from the genotype reaction vessels, is comprised of 250 reaction vessels dedicated for copy number analysis or real-time PCR testing. These vessels receive copy number reagents by way of micro-channels coupled to the receiving cells of region 43. In this way, reagents specific to the type of genetics testing are spatially mapped to particular cells of the reaction portion of the platform. In a final critical arrangement, reaction vessels elements 46 is optically coupled to a detection system appropriate for genotype testing and reaction vessels array 47 is optically coupled to a detection system most appropriate for copy number analysis. It will be understood that despite the appearance of the diagram which does not show the micro-channels for all receiving cells, such micro-channels nevertheless do couple receiving cells to reaction vessels.

Figure 5:
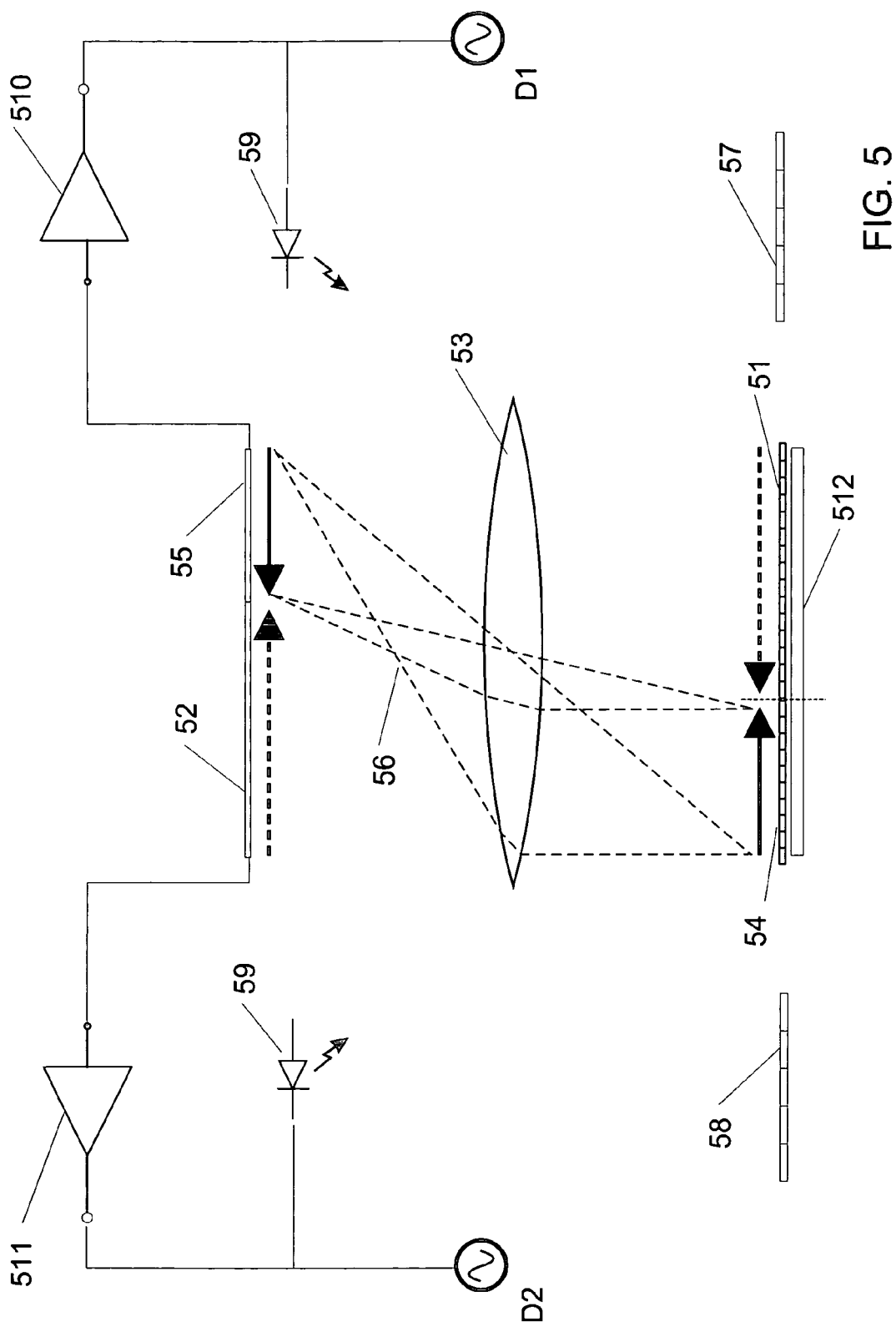
FIG. 5 illustrates dual optical detection systems spatially multiplexed to various portions of a dual mode platform of these systems shown in a cross section view.

FIG. 5 is provided to disclose details of special optical systems of these dual-mode microfluidic testing platforms. Of course, the previous diagrams clearly show how reagents specific to the two types of genetics testing are coupled to the reaction vessels in a manner whereby the reagents are easily mapped to the reaction vessels array, those diagrams do not suggest how spatial separation cooperates with the distinct detector strategies associated with genotype testing versus real-time PCR (copy number analysis). As described previously herein, a detector suitable for copy number analysis requires an electronics driver system coupled to the thermocycler which makes a plurality of intensity measurements—one each for each thermal cycle in preferred systems. Conversely, driver electronics for genotype test detection only need a single measurement at the end of a plurality of applied thermal cycles. However, in some genotyping schemes, a plurality of wavelengths may be necessarily used and a genotype detector must operate in view of chromatic distinctions which may sometimes be present. Optical detectors coupled to copy number analysis regions of the array may be color blind.

Accordingly, these distinct detector characteristics must be respected in view of the spatial separation of reaction vessels dedicated to each type of genetics test. To effect this, an example imaging system is illustrated in FIG. 5. Reaction vessels 51 associated with genotype testing are imaged at image plane portion 52 by lens 53 which maintain spatial integrity between object and image planes. Likewise, reaction vessels 54 associated with copy number testing are imaged at image plane portion 55. This is better understood by the ray trace 56 diagram well known in the optical arts. The image plane may share space with optical detectors such as a silicon photodiodes or the more sophisticated CCD type pixel imagers. For geometric reference and comparison with earlier presented figures, DNA sample receiving cells 57 and reagent receiving cells 58 are shown aside of the reaction vessels array (51 and 54). Two distinct electrical drivers D1 and D2 are coupled to illumination systems 59 and distinct detector plane image elements by way of amplifier 510 and amplifier 511. Driver D1 is arranged to illuminate the object plane for each thermal cycle applied by the thermocycler 512 or more precisely, a polymerase chain reaction PCR thermal cycler. In addition, the driver D1 is arranged to measure the optical intensity at each image element in the image plane that is associated by spatial relationship with a reaction vessel which supports copy number genetics testing. Accordingly, each optical detector of this portion of the detection system has a high dynamic range.

Similarly, driver D2 is arranged to illuminate, reaction vessels having therein genotype test chemistry. Although a plurality of distinct chromatic measurements may be made, genotype detection only requires intensity measurements be made after all required thermal cycles have been executed. Thus D2 is arranged to illuminate the object plane and read signals from a CCD in a single measurement operation which occurs after the thermal cycle schedule is completed. In this way, a single physical platform is multiplexed whereby spatially distinct regions permit optical coupling to two different detection systems arranged to make specific measurements, further whereby mechanical arrangement of microfluidic channels permit receipt of two types of test chemistry for reagent multiplexing, and further whereby the platform may be thermally coupled to a single thermocycler system where required thermal cycling for both types of genetics test may be applied simultaneously.

Figure 7:
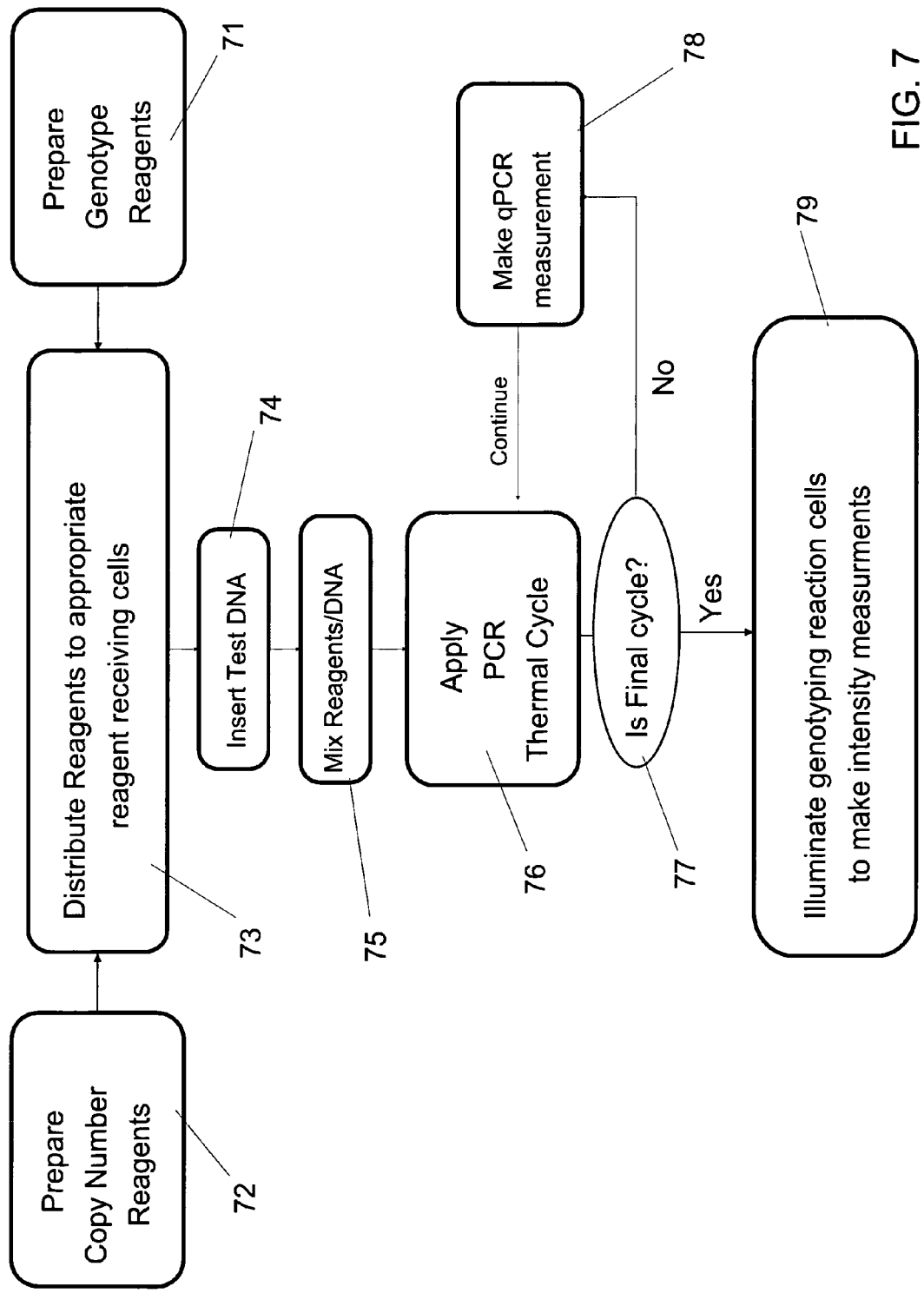
FIG. 7 is a block diagram setting forth major elements of methods of these systems including relationships therebetween same elements.

It should be appreciated that the spatial arrangements illustrated in FIG. 3 and FIG. 4 are not sacred. It is entirely possible and anticipated that other arrangements including random distributions are possible. FIGS. 6A to 6D is provided to illustrate. FIG. 6A shows a uniform 25×25 distribution of reaction vessels of a microfluidic array genetics test platform. Stippling is provided to indicate those cells dedicated to copy number analysis and those allocated to genotype testing. Vertical stippling in 250 cells of the left side are those copy number reaction vessels, while 375 cells on the right half of the platform comprise reaction vessels of genotype configuration in agreement with earlier presented figures. However FIG. 7B shows an important alternative. Cells randomly distributed about the array have vertical stippling to indicate their type as a copy number test cells. Similarly, spatially separate a random distribution of cells having horizontal stippling indicate those cells provided for genotype testing. When drawn separately, FIG. 6C shows genotyping reaction vessels in FIG. 6D shows copy number analysis cells. Because a detection system comprised of discrete picture elements is easily aligned with the test platform described as such having a plurality of spatially distinct cells, it only requires a careful mapping in software to drive the detector in an appropriate fashion for both types of testing. Nevertheless, optical signals are read from the copy number test cells throughout the thermal cycles—either between each cycle or between each set of several cycles to effect a plot as shown in FIG. 2 which is necessary for copy number analysis.

While apparatus of these systems were fully and thoroughly presented in the description previous, methods of these systems follow closely and may be further characterized as follows. In a first step, chemistry appropriate for genotype measurements is prepared 71. This may include chemistry sometimes known as TaqMan. These TaqMan probes include optically activated markers attached to genetic fragments where the sequence of the genetic fragment is a combination of particular interest. In some versions, more than one color of optical marker may be used and sometimes these are used in to distinguish between major and minor alleles of the same SNP.

Similarly, reagents are prepared 72 in support of a copy number genetics test. These may also be arranged as TaqMan reagents, however color is unimportant. Rather, in copy number analysis schemes a reference sequence of known copy number is included to form an intensity comparison reference. A sequence under test may present a higher density than the reference where the copy number is higher and lower intensity where the copy number is lower. Accordingly, reagents appropriate for copy number testing include this baseline reference.

TaqMan probes for genotyping tests are distinct from those relating to copy number. When performing genotyping tests, certain SNPs are far more interesting than others. The particular nucleotide combinations which define these SNPs of high interest will be embodied as the TaqMan probes of a genotype reagent. However, SNPs which are related to copy number studies are not always the most important SNPs of interest in genotyping. Therefore, TaqMan probes useful in copy number analysis may have different nucleotide sequences that those used for genotyping.

After these two reagent types are prepared, they are distributed 73 to various of the reagent receiving cells in accordance with a prescribed mapping known to the detection system. In a following step, DNA test matter is inserted 74 into receiving cells. Reagents and test DNA together are conveyed from their respective receiving cells via microchannels to reaction vessels of a reaction vessel array and mixed 75 in another step of these methods. After reagents and test DNA are together in respective reaction vessels, a thermocycler applies 76 heat/cooling cycles simultaneously to both types of reaction vessels.

After one cycle, or a prescribed set of cycles are applied, intensity measurements are made at the copy number reaction vessels. A conditional step 77 is executed to determine whether the thermal cycle schedule is completed. If not, a qPCR or real-time PCR measurement 78 is made. Additional thermal cycles are applied and the same conditional is repeated. After all cycles have been applied to reaction vessels and the thermal cycle schedule is complete, a final intensity measurement 79 is made at each genotyping reaction vessel.

In this way, a single platform may be used to simultaneously execute both genotyping and copy number analysis in a single process run. This is particularly important when DNA from a single person is to be subject to both tests. Where microfluidic systems are configured for either test but not the other, then two separate process runs must be executed and this consumes excess resources. Accordingly testing in two separate process runs adds to both complexity and expense. Conversely, when a single microfluidic platform arrange to simultaneously support both types of genetic testing genotyping and copy number analysis, and efficiency is realized and cost savings are made possible.

In accordance with each of preferred embodiments of the invention, dual mode genetics testing apparatus and methods are provided. It will be appreciated that each of the embodiments described include an apparatus and that the apparatus of one preferred embodiment may be different than the apparatus of another embodiment. Accordingly, limitations read in one example should not be carried forward and implicitly assumed to be part of an alternative example.

One will now fully appreciate how single platform microfluidic arrays may be configured and deployed to accomplish copy number variation and genotyping genetic testing in single process runs. Although the present invention has been described in considerable detail with clear and concise language and with reference to certain preferred versions thereof including best modes anticipated by the inventors, other versions are nevertheless possible. Therefore, the spirit and scope of the invention should not be limited by any of the preceding descriptions of preferred versions, but rather by the claims appended hereto.

What is claimed is:

1. A dual mode genetic testing platform comprising:
   a) a microfluidic platform;
   b) a thermocycler system thermally coupled thereto; and
   c) a multi-channel optical detector coupled thereto,
   said microfluidic platform comprising:
   a first analysis module comprising a plurality of first reaction vessels each comprising a contrast enhancing reagent and a first composition of PCR reagents configured for a copy number analysis testing, each of said first reaction vessels being optically coupled to a first channel of the multi-channel optical detector, wherein said first channel further comprises first electronic drivers operable for capturing a plurality of discrete optical signals over the course of an extended period of time;
   a second analysis module comprising a plurality of second reaction vessels each comprising a plurality of distinct optical reporters and a second composition of PCR reagents configured for a genotype testing, each of said second reaction vessels being optically coupled to a second channel of the multi-channel optical detector, wherein said second channel further comprises second electronic drivers configured to capture a single optical signal at a discrete moment in time;
   wherein said microfluidic platform is configured to remain in physical contact with said thermocycler system throughout a prescribed set of thermocycles.

2. The dual mode genetic testing platform of claim 1, said multi-channel optical detector having a charged-coupled device (CCD) with a first channel coupled to reaction vessels of said first analysis module and a second channel coupled to reaction vessels said second module wherein the reaction vessels of the second analysis module are spatially removed from reaction vessels of the first analysis module, whereby separate optical signals may be captured with respect to each module.

3. The dual mode genetic testing platform of claim 1, wherein said first channel is further arranged with driver electronics operable for capturing optical signals of a plurality of wavelengths.

4. The dual mode genetic testing platform of claim 1, wherein said second channel is further arranged with driver electronics which enable the optical detector to detect return optical signal of intensities which range over at least two orders of magnitude.

5. The dual mode genetic testing platform of claim 1, wherein said genetic testing platform further comprises optically activated markers attached to a genetic fragment, wherein nucleotide sequence of the genetic fragment corresponds to a gene of particular interest and wherein said optically activated markers' reemission spectra are affected by proximity of the markers to one another.

6. The dual mode genetic testing platform of claim 5, wherein said genetic testing platform comprises a first and a second optically activated markers, said first optically activated marker attached to a first genetic fragment having a sequence which selectively anneals to a first allele at a locus of interest, said second optically activated marker attached to a second genetic fragment having a sequence which selectively anneals to a region of variable copy number.

7. The dual mode genetic testing platform of claim 6, wherein said second analysis module further comprises a reference nucleic acid molecule capable of annealing with said second genetic fragment to produce an optical signal by which a comparison may be made with respect to alleles under test.

8. The dual mode genetic testing platform of claim 6, wherein said first optically activated marker attached to a first genetic fragment having a sequence which selectively anneals to an allele of a locus of interest is provided with a third optically activated marker attached to a third genetic fragment having a sequence which selectively anneals to a second allele of a locus of interest, and wherein said third optically active marker possess an optical property which is detectably different from said first optically active marker.

9. The dual mode genetic testing platforms of claim 1, wherein at least one of said first reaction vessels and at least one of said second reaction vessels are provided with a common nucleic acid sample.

10. The dual mode genetic testing platform of claim 8, wherein first optically activated marker fluoresces at a first wavelength, wherein said third optically activated marker fluoresces at a third wavelength, and wherein said multi-channel optical detector is configured to distinctly detect said first wavelength and said third wavelength.

11. The dual mode genetic testing platform of claim 1, wherein said contrast enhancing reagent specifically enhances optical signals captured from the first reactions vessels of the first analysis module.

12. The dual mode genetic testing platform of claim 1, wherein said first channel of the multi-channel detector is color blind.

\* \* \* \* \*